United States Patent [19]
Boderie et al.

[11] Patent Number: 5,111,037
[45] Date of Patent: May 5, 1992

[54] DEVICE FOR MEASURING LIGHT SCATTERED BY AN INFORMATION SUPPORT

[75] Inventors: Emile E. M. Boderie; Marinus J. M. Van Dam, both of Venlo, Netherlands

[73] Assignee: Oce Nederland B.V., Netherlands

[21] Appl. No.: 548,119

[22] Filed: Jul. 5, 1990

[30] Foreign Application Priority Data

Jul. 6, 1989 [NL] Netherlands .................. 8901722

[51] Int. Cl.$^5$ ..................... H01J 3/16; G03B 27/74
[52] U.S. Cl. ................... 250/216; 250/237 R; 356/443; 355/68
[58] Field of Search ............ 356/443, 432, 433, 434, 356/435, 445; 250/571, 216, 237 R; 355/68, 214, 242, 246

[56] References Cited

U.S. PATENT DOCUMENTS

| | | | |
|---|---|---|---|
| 3,076,378 | 2/1963 | Biedermann et al. | 356/443 |
| 3,761,726 | 9/1973 | De Cock | 250/571 |
| 3,809,911 | 5/1974 | Natens | 356/443 |
| 3,856,417 | 12/1974 | Bey et al. | 356/443 |
| 4,266,872 | 5/1981 | Mitsuhashi | 356/443 |
| 4,473,298 | 9/1984 | Sakamoto | 356/432 |
| 4,937,764 | 6/1990 | Komatsu et al. | 356/432 |

FOREIGN PATENT DOCUMENTS 0234579  9/1987  European Pat. Off. .

*Primary Examiner*—David C. Nelms
*Assistant Examiner*—Michael Messinger
*Attorney, Agent, or Firm*—Reed Smith Shaw & McClay

[57] ABSTRACT

A device for measuring light scattered by an information support in which a light source is used to expose a portion of the information support. A sensor having a light-sensitive surface and an output signal dependent upon the quantity of light falling on such surface is positioned behind an objective lens disposed between the information support and the sensor. The exposed portion of the information support is smaller than the field of view of the sensor and the sensor is disposed at a distance behind the objective lens where the quantity of light on the light-sensitive surface of the sensor remains constant to within 5% in the event of a variation of ±20% in the distance of the information support from the objective. The light-sensitive surface of the sensor is disposed within the beam of light scattered by the information support and emerging from the objective lens.

5 Claims, 2 Drawing Sheets

DEVICE FOR MEASURING LIGHT SCATTERED BY AN INFORMATION SUPPORT

FIELD OF THE INVENTION

The invention relates to a device for measuring light scattered by an information support in which a light source is used to expose a portion of the information support and a sensor with an output signal dependent upon the quantity of light falling on its surface, is positioned from an objective lens a distance wherein the quantity of light measured by the sensor is within 5% caused by a variation in the displacement of exposed portion of the information support.

BACKGROUND OF THE INVENTION

Various devices have been used to measure light for an information support. For example, U.S. Pat. No. 3,761,726 discloses a photoelectric device in which mirrors are used to focus light from an information support to a sensor. European Application 0 234 579 describes a reflection density measuring system used to monitor chemical assay slides.

In U.S. Pat. No. 4,639,607, a paper edge detector is described in which a beam of light is directed onto a small portion of a reflecting surface. The specular-reflected light from this surface then falls on the detector via a converging lens. Within certain limits the amount of light detected is independent of changes in orientation of the reflecting surface, although the distance between the exposed portion and the lens should stay constant.

A device of this kind can be used, for example, to determine the necessary exposure for background-free copying in an electrophotographic apparatus. To this end, the amount of light scattered by an information support is measured by exposing a portion of this support and measuring the amount of light scattered from the exposed portion. A disadvantage of this is that if there is any change in the distance between the information support and the sensor, the amount of light on the sensor may change. This occurs, for example, if the information support moves in a path along the sensor with possible variation of the positioning of the information support with respect to the sensor. Accordingly, it is an object of this invention to substantially reduce the disadvantage.

SUMMARY OF THE INVENTION

Generally, the invention provides a sensor disposed at a distance behind the objective where the quantity of light on the light-sensitive surface of the sensor remains constant to within 5% in the event of a variation of ±20% in the distance of the information support from the objective. The maximum linear dimension L of the light-sensitive surface of the sensor satisfies the following equation:

$$L < \frac{fA + fB - AB}{fA} \cdot d_{lens}$$

Where
A denotes the distance between the information support and the objective,
B is the distance between the objective and the light-sensitive surface of the sensor,
f the focal length of the objective, and
$d_{lens}$ is the effective diameter of the objective.

It has been found that there is an optimal position for the sensor in which the amount of light on the light-sensitive surface of the sensor remains constant or substantially constant in the event of any variation—within wide limits—of the distance between the information support and the objective. This optimal position is dependent inter alia on the distance between the information support and the objective, the focal length of the objective, the size and shape of the light-sensitive surface of the sensor and the scattering properties of the information support.

For some embodiments it is possible to calculate the optimal position of the sensor if the above parameters are known. In many cases, however, the calculation is so complex that it is in practice simpler to determine the optimal position by experiment. For example, the sensor is positioned at 110% of the focal length behind the objective. The output signal of the sensor is determined as a function of the shift of the information support with respect to the objective over the required length in which the quantity of light incident on the sensor must remain constant or substantially constant. The sensor is moved stepwise in the direction of the objective and the output signal of the sensor is determined for each step as a function of the shift of the information support with respect to the objective over the required length. In this way it is a simple matter to determine the position where the quantity of light incident on the sensor is sufficiently constant for the required application in the event of a shift of the information support with respect to the lens.

It has also been found that if the information support scatters light diffusely and the length and width of the light-sensitive surface of the sensor are equal or substantially equal then it is possible to calculate the optimal position of the sensor. The amount of light incident on the sensor in the event of a shift of the information support with respect to the lens is substantially constant if the distance A between the information support and the objective, the distance B between the objective and the light-sensitive surface of the sensor, the focal length f of the objective and the size M of the light-sensitive surface are so selected as to satisfy or substantially satisfy the following equation:

$$\frac{2\sqrt{2}}{\pi} \cdot \frac{AM}{(M + 4A^2)\sqrt{M + 2A^2}} = \frac{fB}{fA + fB - AB} \cdot \left[1 - \frac{4}{\pi} \cdot \arcsin\frac{\sqrt{2} \cdot A}{\sqrt{M + 4A^2}}\right]$$

If A, M and f are known, it is possible to calculate the sensor position B on the basis of the above equation. This calculated sensor position can be used as a starting value for experimental optimization of the sensor position as described above if, for example, a different sensor form is used or if the information support does not completely scatter the light diffusely.

Other features and advantages of the invention will be clear from the following description with reference to the accompanying drawings

PRESENTLY PREFERRED EMBODIMENTS

Figure 1:
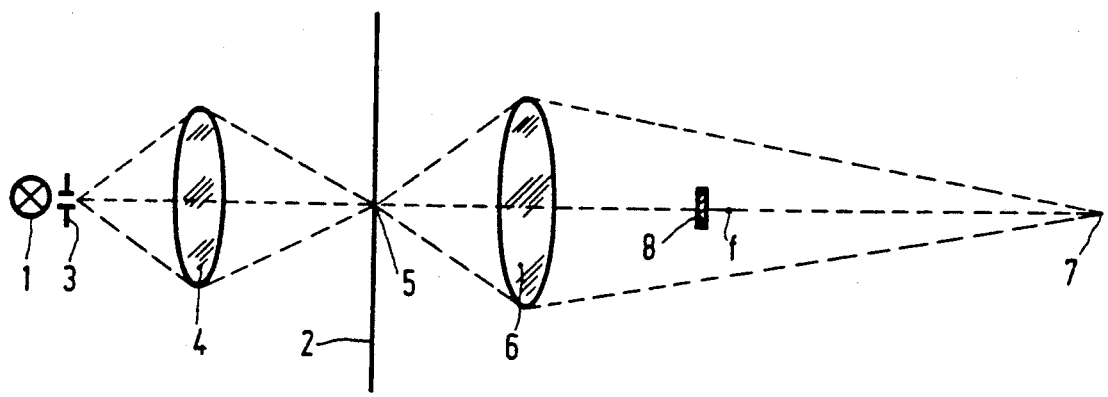
FIG. 1 is a diagram of an embodiment of a device according to the invention.

FIG. 1 diagrammatically illustrates an embodiment of a device according to the invention usable for measuring in transmission the quantity of scattered light from a completely diffuse-scattering information support, in which light is focussed on an information support 2 by means of light source 1. For this purpose, a pinhole 3 is disposed in the vicinity of the light source 1. The light from the resulting point source is imaged on a small surface 5 of the information support 2 via a converging lens 4. The diffuse-scattered light from the information support 2 is imaged at point 7 by means of the converging lens 6. A light-sensitive sensor B is disposed in the path of the light between the converging lens 6 and image point 7 in front of the focal point f of the converging lens 6. The location of the sensor B is so selected that in the event of any change within a few mm in respect of the distance between the information support 2 and the converging lens 6 and the sensor S the quantity of light on the sensor S remains substantially constant. The entire light-sensitive surface of the sensor S comes within the beam of light converging at point 7 as a result of lens 6. Given a distance of 1 cm between the information support 2 and the converging lens 6, a focal length of 8 mm, a square effective sensor area of 4 mm$^2$ and a lens diameter of 50 mm the optimal sensor position is 7.9 mm from the lens 6. The amount of light on the sensor 8 is constant to within 0.2% in the event of any variation in the distance between the information support 2 and the lens 6 ranging from 0.8 to 1.2 cm.

Figure 2:
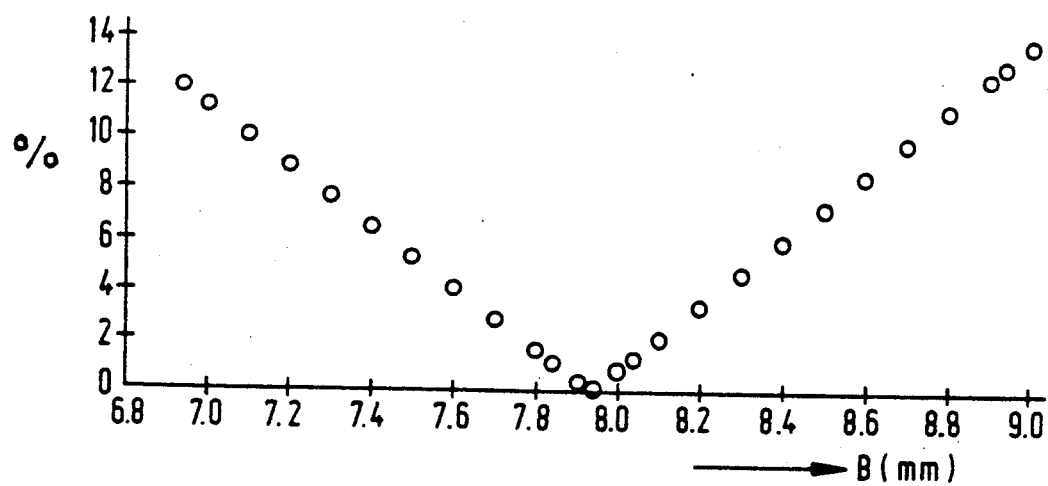
FIG. 2 shows the percentage change of the quantity of light on the sensor in the event of a variation of ±20% the distance between the information support and the objective as a function of the distance between the objective and the sensor in the embodiment shown in FIG. 1.

With any other distance between the sensor 8 and the lens 6 in the above embodiment, the amount of light is much less constant in the event of a change in the distance between the information support 2 and the lens 6 over a length of 4 mm. The percentage change over that length of the amount of light on the sensor S as a function of the distance between the lens 6 and the sensor B is shown in FIG. 2. This also shows that if the sensor is shifted 1 mm from the optimal sensor position (either in the direction of the lens 6 or away from the lens 6) the quantity of light on the sensor B varies approximately 12% if the distance between the information support 2 and the lens 6 is varied over a length of 4 mm.

Figure 3:
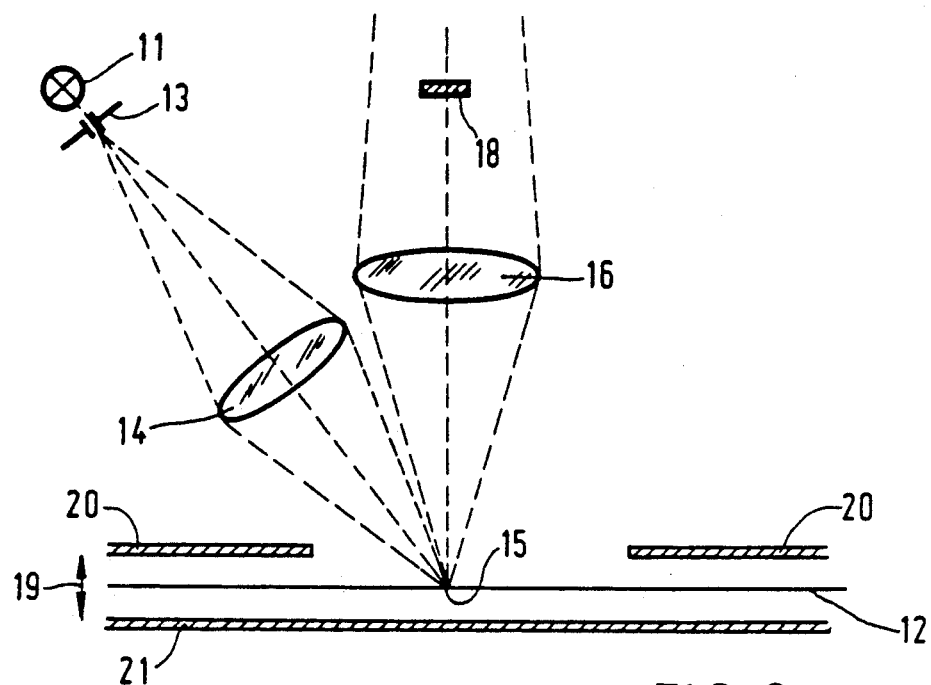
FIG. 3 diagrammatically illustrates another embodiment of the invention.

FIG. 3 shows another embodiment in which the device according to the invention is used for measuring the amount of scattered light in reflection from an information support 12, the latter being situated in a path 18 through which the information support 12 is fed past the device. During the measurement the information support 12 is situated within the boundaries 20,21 of said path 19, so that the distance between the information support 12 and the lens 16 can vary within the boundaries 20, 21 of the path 19.

By means of a light source 11 provided with a pinhole 13 a small portion 15 of the information support 12 is illuminated in incident light. For this purpose, the light is focussed in the middle of the path 19 by means of a lens 14. Given a distance of 1 cm between the information support 12 and the converging lens 16, a focal length of 10 mm, a square effective 1, light-sensitive area of the sensor 18 of 10 mm$^2$ and a lens diameter of 50 mm, the sensor position is 9.7 mm from the lens 16. Given a variation in the distance between the information support 12 and the lens 16 ranging from 0.8 to 1.2 cm, the amount of light on the sensor 18 is constant to within 1%. In these conditions the angle between the optical axis of the lighting channel and the information support 12 is moved out of the center of the path 19, the light spot 15 moves with respect to the optical axis of the measuring channel. This greatly influences the total amount of light on the sensor 18. In order to keep the amount of light on the sensor 18 as constant as possible, the angle between the optical axis of the lighting channel and the optical axis of the measuring channel should be as small as possible. However, in the case of a very small angle, there is a risk that specular-reflected light will meet the sensor 18. Measurements have shown that the sensitivity to variations of the position of the information support 12 with respect to the lens 16 is about ten times as small with an angle of 25° than with an angle of 45°, while the risk of specular reflection is still low with an angle of 25°.

Figure 4:
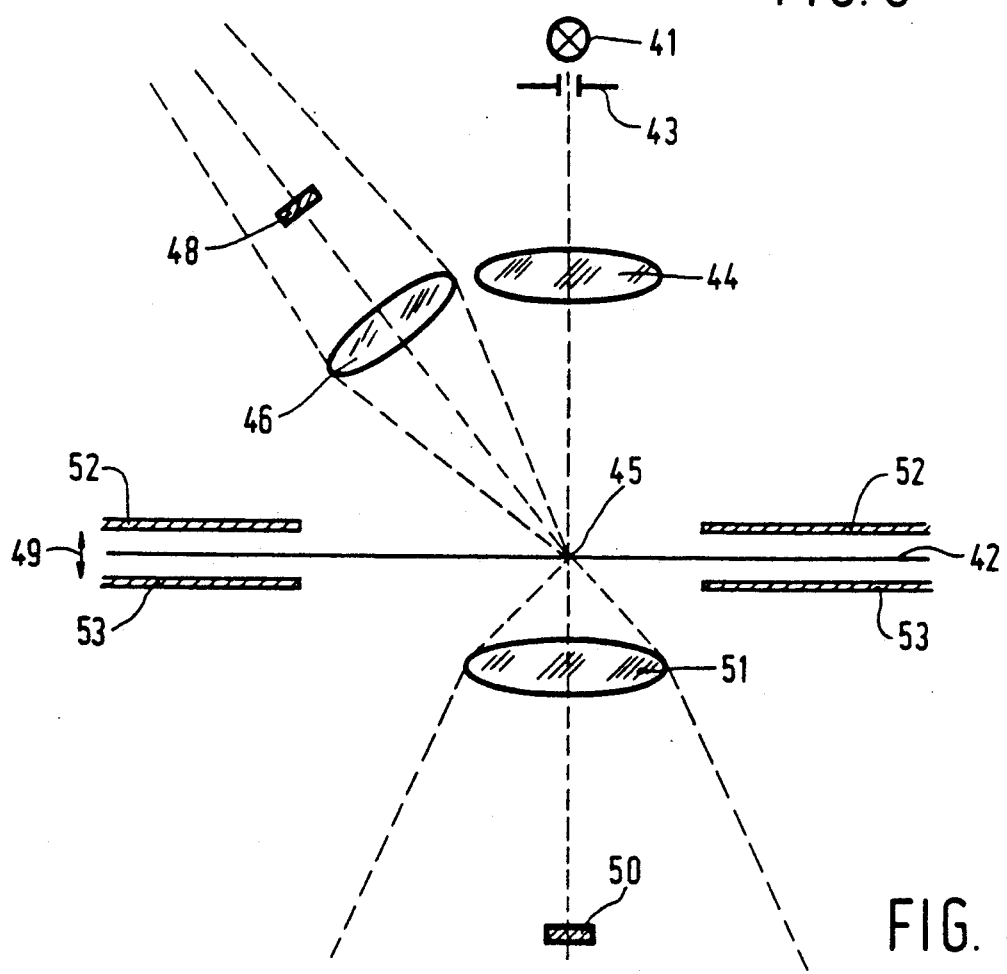
FIG. 4 diagrammatically illustrates a yet another embodiment of the invention.

FIG. 4 shows another embodiment in which the device according to the invention is used for measuring the amount of reflected and transmitted light scattered by an information support 42. A single light source 41 is used in this case, with a pinhole 43 disposed in the vicinity of the light source 41. The light of the resulting point source is imaged on a small surface 45 of the information support 42 via a converging lens 44, by focussing the light in a point in the middle of the path 49 through which the information support 42 is fed past the device.

This embodiment uses a sensor 48 on the same side of the information support 42 as the light source 41 for measuring the quantity of reflected light, a converging lens 46 being disposed between the sensor 48 and the path 49 and a second sensor 50 on the other side of the information support for measuring the quantity of transmitted scattered light, a converging lens 51 being disposed between the sensor 50 and the path 49. During the measurement the information support 42 is situated within the boundaries 52, 53 of the path so that the distance between the information support 42 and the lenses 46, 51 can vary within the boundaries 52, 53 of the path 49.

This embodiment uses a pinhole 43 of a diameter of 1 mm. The distance between the center of the path 49 and the lens 51 is 5 mm. The distance between the center of the path 49 and the lens 46 is 10 mm. The biconvex lenses 44, 46, 51 all have a focal length of 10 mm and a diameter of 50 mm. The sensors have an effective light-sensitive area of 4 mm$^2$. The distance between the sensor 50 and the lens 51 is 9.2 mm. The distance between the sensor 48 and the lens 46 is 9.9 mm. Given a variation of ±20% in the distances of the information support from the lenses 46, 51, the quantity of light on the sensors 48, 50 is constant within 1%.

This latter embodiment can be used, for example, in an electrophotographic apparatus in which, inter alia, translucent originals copied. The optimal exposure for suppressing the background on the copy and/or the correct contrast can be controlled, automatically if required, on the basis of the reflection and transmission properties determined by means of the device according to the invention. From the measured quantities of reflected and transmitted scattered light it is then possible to select either incident light exposure alone, transmitted light exposure alone, or a combination of both, the total quantity of light and the mutual relationship of the intensities of the incident light lamps and the transmitted light lamps being variable.

In the described embodiments with respect to FIGS. 1, 3 and 4, lamps 1, 11, and 41, respectively, were used for the exposure together with pinholes 3, 13, and 43, respectively, converging lens 4, 14, and 44 being disposed between information supports 2, 12, and 42 and lamps 1, 11, and 41 so that the light was focussed on the information supports 2, 12, and 42, respectively. Other light sources, e.g., light-emitting diodes, lasers and the like, by means of which focussed light can be projected on the information support and with which the size of the light spot on information supports 2, 12, and 42 remains constant or substantially constant in the event of any shift of information supports 2, 12, and 42, are also usable. When used in an electrophotographic apparatus to measure the brightness of the background of an original, it is advantageous to make the exposed portion as small as possible so that any information present on the original has the minimum possible influence on the measurement.

It has been found that the presence of folds or creases in the information support is unfavorable with regard to the constant value of the amount of light measured, particularly if it is measured in reflection. It has been found advantageous so to position the embodiments of the device according to the invention as shown in FIGS. 3 and 4 that the plane defined by the optical axes of the exposure channel and the measuring channel is perpendicular to the direction of transport of the information support. In the event of folds perpendicular to the direction of transport, when the fold passes the device the measuring signal will show a fall-off.

In determining the exposure required in order to obtain copies free of any background however, use is made of the maximum measuring signal so that such folds do not have an adverse effect on the operation of the device.

While presently preferred embodiments of the invention have been shown and described in particularity, the invention may be otherwise embodied within the scope of the appended claims.

What is claimed is:

1. A device for measuring light scattered by an information support comprising:
   (a) a light source directed to said information support;
   (b) at least one objective lens to focus light from said information support; and
   (c) at least one sensor having a light-sensitive surface for sensing light from said information support and positioned from said objective lens a distance wherein the light-sensitive surface lies within a beam of focussed light from said objective lens and senses a fraction of said focussed light whereby the quantity of light sensed remains substantially constant over a variation of ±20% in distance between said information support and objective lens.

2. A device as set forth in claim 1, wherein said distance from said sensor and said objective lens is predetermined such that said quantity of light remains constant to within 5% in the event of any such variation.

3. A device as set forth in claim 1, including a second objective lens and a second sensor positioned on a side of said information support opposite said at least one objective lens and said at least one sensor, said second objective lens serving to focus light from said information support and said second sensor having a light-sensitive surface for sensing light from said information support and positioned from said second objective lens a distance wherein the light-sensitive surface thereof lies within a beam of focussed light from said second objective lens and senses a fraction of said focussed light therefrom whereby the quantity of light sensed by said second sensor remains substantially constant over a variation of ±20% in distance between said information support and said second objective lens.

4. A device for measuring light scattered by an information support comprising:
   (a) a light source for exposing at least a portion of said information support;
   (b) an objective lens for directing light from said information support to a sensor; and
   (c) a sensor having a light-sensitive surface and an output signal dependent upon the quantity of light falling on the light-sensitive surface from said objective lens; said sensor being disposed at a distance behind said objective lens wherein the light-sensitive surface lies within a beam of focussed light from said objective lens and senses a fraction of said focussed light whereby the quantity of light on the light-sensitive surface of the sensor remains constant to within 5% in the event of a variation of ±20% in the distance of said information support from the objective, and a maximum linear dimension L of said light-sensitive surface of said sensor satisfies the following equation:

$$L < \frac{fA + fB - B}{fA} \cdot d_{lens}, \text{ where}$$

A is the distance between said information support and the objective lens;

B is the distance between said objective lens and said light-sensitive surface of the sensor;

f is the focal length of said objective lens; and $d_{lens}$ is the effective diameter of said objective lens.

5. A device according to claim 4, in which the length and the width of said light-sensitive surface of the sensor are substantially equal to one another and wherein said distance A between said information support and said objective lens, said distance B between the said objective lens and said light-sensitive surface of said sensor, said focal length f of the objective lens and the size M of the light-sensitive surface are so selected as to substantially satisfy the relationship:

$$\frac{2\sqrt{2}}{\pi} \cdot \frac{AM}{(M + 4A^2)\sqrt{M + 2A^2}} = \frac{fB}{fA + fB - AB} \cdot \left[1 - \frac{4}{\pi} \cdot \arcsin \frac{\sqrt{2} \cdot A}{\sqrt{M + 4A^2}}\right]$$

* * * * *